United States Patent [19]

Phillipps et al.

[11] 4,451,405
[45] May 29, 1984

[54] 11α-AMINO-3β-HYDROXY-ANDROSTANES

[75] Inventors: Gordon H. Phillipps, Wembley; David C. Humber, Ealing; David B. Ewan, Northolt; Barry A. Coomber, Pinner, all of England

[73] Assignee: Glaxo Group Limited, London, England

[21] Appl. No.: 447,190

[22] Filed: Dec. 6, 1982

Related U.S. Application Data

[63] Continuation of Ser. No. 353,068, Mar. 1, 1982.

[30] Foreign Application Priority Data

Mar. 2, 1981 [GB] United Kingdom ............... 8106486

[51] Int. Cl.³ .......................................... A61K 31/56
[52] U.S. Cl. .............................................. 260/397.1
[58] Field of Search ................................... 260/397.1

[56] References Cited

FOREIGN PATENT DOCUMENTS 1581234 12/1980 United Kingdom ........... 260/397.45
1581235 12/1980 United Kingdom ........... 260/397.45

Primary Examiner—Elbert L. Roberts
Attorney, Agent, or Firm—Bacon & Thomas

[57] ABSTRACT

Compounds of the formula

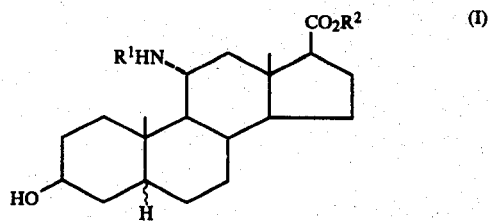

wherein $R^1$ is a $C_{1-8}$ alkyl group or a $C_{3-7}$ cycloalkyl group, and $R^2$ is a $C_{1-6}$ alkyl group or a $C_{3-6}$ cycloalkyl group and the D-homo analogues thereof having the group —$CO_2R^2$ (wherein $R^2$ is as defined above) at the 17αβ-position, and acid addition salts thereof have activity as antidysthythmic agents and may be applicable for the treatment of dysrthymias in humans or animals. The compounds may be provided in the form of compositions in admixture with pharmaceutical carriers and excipients and may be prepared by a variety of processes known for producing steroids of this type. The invention also provides intermediates for the preparation of the compounds of formula (I) wherein $R^2$ and/or $R^1$ are replaced with hydrogen atoms, and processes for the preparation of such intermediates.

13 Claims, No Drawings

11α-AMINO-3β-HYDROXY-ANDROSTANES

This application is a continuation of application Ser. No. 353,068 filed Mar. 1, 1982.

This invention relates to aminosteroids having antidysrhythmic activity, and in particular to certain compounds in the androstane series having a substituted or unsubstituted amino group at the 11α-position and a hydroxy group at the 3β-position.

The aim of antidysrhythmic therapy is to return hazardous abnormal heart rhythms towards normal, or to reduce the likelihood of hazardous rhythms developing in patients at risk as a result of hypertension, atheromas, diabetes or heart conditions such as myocardial disease, ischaemia or infarction.

It is recognised that dysrhythmias in patients with heart attack and other conditions are treatable and preventable. There are several drugs available for the treatment of ventricular dysrhythmias but their application is limited by their lack of efficacy or by their toxicity which gives rise to various side effects.

Thus there is a demand for drugs suitable for use in the treatment of patients with dysrhythmias, and therefore in danger of sudden cardiac death. Furthermore, there is a demand for such drugs for administration, for example for long term prophylaxis, to patients at risk of developing dysrhythmias, in which case, activity on oral administration is desirable.

In Belgian Patent Specification No. 853227 there is described a group of 11α-tertiaryr amino-3α-hydroxy steriods having anaesthetic activity. In addition to the 11α-tertiary amino and 3α-hydroxy groups, the possibility of the compounds possessing various substituents in other positions including the 17β-position is allowed for, one possible 17β-substituent being a $C_{1-5}$ alkoxycarbonyl group. Corresponding 11α-primary and secondary amino steroids are also described as intermediates for the preparation of the tertiary amino compounds. There is no specific disclosure in Belgian Patent No. 853227 of any 11α-primary or secondary amino-17β-alkoxycarbonyl compounds, and no anaesthetic activity is ascribed to any such compounds specifically. Furthermore, no antidysrhythmic activity has been ascribed to any of the compounds in the above Belgian Patent Specification, or indeed to any compounds of comparable structure.

We have now discovered that a group of steroids having a primary or secondary amino group at the 11α-position and a 3β-hydroxy group have promising antidysrhythmic activity.

Accordingly the invention provides 11α-amino-3β-hydroxy-androstanes of the formula

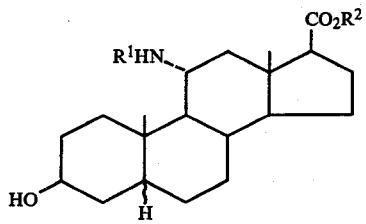

wherein
$R^1$ is a $C_{1-8}$ alkyl group or a $C_{3-7}$ cycloalkyl group and
$R^2$ is a $C_{1-6}$ alkyl group or a $C_{3-6}$ cycloalkyl group and
the D-homo analogues thereof having the group $-CO_2R^2$ (wherein $R^2$ is as defined above) at the 17aβ-position, and acid addition salts thereof.

The compounds of the invention have been found to possess useful antidysrhythmic activity in the tests which have been carried out, and have potential as antidysrhythmic drugs.

The 5-hydrogen atom may be in the α- or β-configuration.

Where either of the groups $R^1$ and $R^2$ is an alkyl group it may be straight or branched chain.

Where $R^1$ is a cycloalkyl group, it may be, for example, a cyclobutyl, cyclopentyl, cyclohexyl or cycloheptyl group.

Where $R^1$ is an alkyl group it preferably has 3-7 carbon atoms, and may, for example, be a propyl, butyl, pentyl, isopentyl, hexyl, isohexyl or neohexyl group.

Where $R^2$ is a cycloalkyl group it may be, for example, a cyclopropyl, cyclobutyl, cyclopentyl or cyclohexyl group. Where $R^2$ is an alkyl group, it may be, for example, a methyl, ethyl, propyl, isopropyl, butyl or isopentyl group. $R^2$ is preferably a $C_{1-3}$ alkyl group.

Where compounds having good activity following oral administration are desired, $R^2$ is preferably a methyl or ethyl group.

Particularly preferred compounds are those in which $R^1$ is an isopentyl, hexyl, isohexyl, neohexyl, cyclopentyl or cyclohexyl group and $R^2$ is a methyl or ethyl group, especially a methyl group. The compounds preferably contain a 5α-hydrogen atom.

Ring D conveniently has 5 members.

The compounds of formula (I) may form acid addition salts; physiologically acceptable acid addition salts are preferred.

Examples of acid addition salts are hydrochlorides, hydrobromides, phosphates, sulphates, p-toluenesulphonates, methanesulphonates, citrates, tartrates, acetates, ascorbates, lactates, maleates, succinates, tricarballylates, glutarates and glutaconates. The hydrochlorides are preferred acid addition salts.

Individual compounds which are preferred on the basis of their high antidysrhythmic activity include:
1. Methyl 3β-hydroxy-11α-(3-methylbutylamino)-5β-androstane-17β-carboxylate;
2. Methyl 3β-hydroxy-11α-(3-methylbutylamino)-5α-androstane-17β-carboxylate;
3. Methyl 11α-cyclopentylamino-3β-hydroxy-5α-androstane-17β-carboxylate;
4. Methyl 11α-cyclohexylamino-3β-hydroxy-5α-androstane-17β-carboxylate; and
5. Methyl 11α-cyclohexylamino-3β-hydroxy-5β-androstane-17β-carboxylate and their physiologically acceptable acid addition salts, e.g. their hydrochlorides.

A particularly preferred compound is No. 2 and its physiologically acceptable acid addition salts, e.g. its hydrochloride.

The invention further provides compounds of formula (I), D-homo analogues thereof and physiologically acceptable acid addition salts thereof for use in a method of treatment of the human or animal, in particular mammalian, body to combat cardiac dysrhythmias therein. The invention also provides compounds of formula (I), D-homo analogues thereof and physiologically acceptable acid addition salts thereof in association with instructions for their use as antidysrhythmic agents.

The compounds may be used in the treatment of patients with disturbances of cardiac rhythm, whether arising spontaneously, or as a result of treatment with other drugs, e.g. cardiac glycosides, or as a consequence of myocardial ischaemia or infarction. Alternatively they may be used for the prophylactic treatment of patients at risk of cardiac rhythm disturbances or sudden coronary death.

Accordingly, the invention provides methods of therapy or prophylaxis of a human or animal, in particular mammalian, body suffering from or liable to cardiac dysrthythmias which method comprises administering to the said body an effective amount of a compound of formula (I), a D-homo analogue thereof or a physiologically acceptable acid addition salt thereof.

As a further aspect of the invention there are provided compounds of the formula

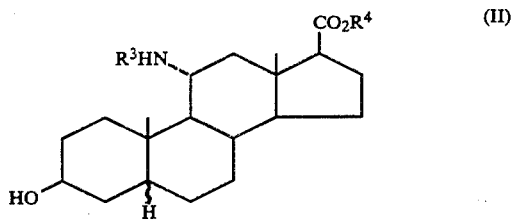

(II)

wherein $R^3$ is a hydrogen atom, a $C_{1-8}$ alkyl group or a $C_{3-7}$ cycloalkyl group, and $R^4$ is a hydrogen atom, a $C_{1-6}$ alkyl group or a $C_{3-6}$ cycloalkyl group with the proviso that at least one of $R^3$ and $R^4$ is a hydrogen atom and the D-homo analogues thereof having the group —$CO_2R^4$ (wherein $R^4$ is as defined above) at the 17aβ-position, and salts and zwitterionic forms thereof.

The compounds of formula (II) may form acid addition salts. The compounds of formula (II) in which the group —$CO_2R^4$ represents a carboxyl group may also form salts with bases or exist as zwitterions.

Examples of acid addition salts are those given above in connection with the compounds of formula (I). The salts with bases may be salts with inorganic bases such as alkali metal salts, e.g. sodium, potassium and lithium salts; alkaline earth metal salts, e.g. calcium and magnesium salts; and ammonium salts, or salts with organic bases for example amine salts.

Compounds of formula (II) are useful as intermediates in the preparation of compounds of formula (I) using the methods described hereinafter.

The compounds of the invention may be prepared by a number of different methods, using generally known techniques. Suitable methods are described below:

1. A substituent on the 11α-amino function may be introduced by reacting the corresponding 11α-amino compound, i.e. a compound of formula (II) in which $R^3$ is hydrogen, with a compound of the formula $R^1X$ wherein X is a readily displaceable atom or group such as halide (e.g. iodide), a hydrocarbylsulphonyloxy group (e.g. toluene-p-sulphonyloxy), a hydrocarbyloxysulphonyloxy group (e.g. methoxysulphonyloxy) or a dialkoxyphosphonyloxy group (e.g. dimethoxyphosphonyloxy). When carried out on compounds of formula (II) in which $R^4$ is also hydrogen, such a reaction may result in esterification to form a compound in which $R^1=R^2$. The group $R^2$ may, if not desired in the final product, subsequently be replaced by transesterification in one or more stages, for example as set out under 8 below. However, where $R^4$ is hydrogen and the initial product is a carboxylic acid, this should be esterified for example as set out under 6 below. The introduction of the substituent on the 11α-amino function is preferably carried out in the presence of a base (e.g. potassium carbonate or silver oxide) in solution at any suitable temperature from ambient to reflux (e.g. +20° to +100° C.). The reaction is conveniently effected in a suitable reaction solvent. Suitable solvents include ethers (e.g. dioxan), substituted amides (e.g. N,N-dimethylformamide or N,N-dimethylacetamide), sulphoxides (e.g. dimethylsulphoxide), alkanols (e.g. ethanol or methanol) or acetonitrile.

When X is a chlorine or bromine atom, the reaction may be facilitated by addition of an iodide such as sodium iodide.

Compounds of formula (II) wherein $R^3$ is hydrogen may be prepared by reduction of the corresponding 11-oxime. Such a reduction may be effected with an alkali or alkaline earth metal in an alcohol and/or an amine and/or ammonia, e.g. sodium in n-propanol, if desired in the presence of a suitable solvent, e.g. tetrahyrofuran, at any suitable temperature up to and preferably at reflux.

The 11-oximes may themselves be prepared from the corresponding 11-oxo compounds. The 11-oxo compound may for example be reacted with hydroxylamine under strongly alkaline conditions in aqueous alcohol (e.g. ethanol), preferably at reflux. The reaction may also be carried out under acidic conditions (ca. pH 4), e.g. in buffered pyridine.

The severe conditions used in the reduction of the 11-oxime make it desirable that the 17β-alkoxycarbonyl substituent should be introduced after the formation of the 11α-amino group.

2. A corresponding 11α-amino compound, i.e. a compound of formula (II) in which $R^3$ is hydrogen, can be reductively "alkylated" with an appropriate monocarbonyl compound in the presence of a reducing agent, the term "alkylated" being used to refer to the introduction of a cycloalkyl group as well as an alkyl group. The reducing agents which may be used are those generally known for the reduction of imines, examples being formic acid (e.g. at any suitable temperature up to 100°-120° C., for example from room temperature up to 100°, and using the carbonyl compound as the reaction solvent, in the presence or absence of water), an alkali metal borohydride or cyanoborohydride (e.g. sodium borohydride or cyanoborohydride, using an alcohol such as ethanol as solvent, suitably at room temperature), iron pentacarbonyl or an alkali metal hydrogen iron carbonylate (e.g. $Fe(CO)_5$ or $MHFe(CO)_4$ where M is sodium or potassium, at any suitable temperature up to reflux using an ether such as tetrahydrofuran or an alcohol or aqueous alcohol as solvent), hydrogen in the presence of a metal catalyst (using an alcohol, e.g. ethanol, an ether, e.g. dioxan or an ester, e.g. ethyl acetate, as reaction solvent, conveniently at room temperature), or aluminium amalgam in the presence of water (conveniently at room temperature, and in the presence of an ether solvent such as tetrahydrofuran).

The metal catalyst may, for example, be a noble metal catalyst such as platinum, platinum oxide, palladium or rhodium. The catalyst may be supported, e.g. on charcoal or kieselguhr. A homogeneous catalyst such as tristriphenylphosphine rhodium chloride may also be used. If desired the intermediate imino compound may be isolated. Thus, for example, the use of formaldehyde, acetaldehyde, 3-methylbutanal or cyclohexanone can provide the 11α-N-methyl, N-ethyl, N-iso-pentyl or N-cyclohexyl amines respectively.

It will be appreciated that the conditions should be chosen to given predominantly the desired N-monosubstituted compound, and minimise production of the corresponding N,N-disubstituted compound. Reductive alkylation of the compounds of formula (II) in which $R^4$ is a hydrogen atom is preferably effected under basic conditions.

Where $R^4$ is hydrogen, the initial product will be a carboxylic acid which should then be esterified to form an ester according to the invention, for example as set out in 6 below.

3. 5β-Steroids of the invention may be prepared from appropriate 3-oxo compounds by stereospecific reduction, e.g. by the method of Browne and Kirk (J.Chem.Soc. C, 1969, 1653) or by using the iridium catalyst reduction system described in our British Patent Specification 1409239. For example, a reduction system may be prepared from an iridium acid or salt (e.g. chloroiridic acid), a trivalent phosphorus compound such as a phosphorous acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system is preformed by heating at reflux, e.g. for 16 to 72 hours, the reduction can be accomplished for example in 2–3 hours at reflux; longer times may be necessary at room temperature.

The 3-oxo 5β-compounds may be prepared by oxidation (e.g. using Jones reagent), of the corresponding 3α-hydroxy 5β-compounds.

4. 3β-Hydroxy 5α-steroids may be prepared by hydride reduction of the corresponding 3-oxo 5α-compound. The hydride reducing agent is preferably an alkali metal borohydride or cyanoborohydride such as sodium borohydride or cyanoborohydride, using an alcohol (e.g. methanol or ethanol) or pyridine as solvent. The reaction is conveniently carried out in the temperature range 10° to 40° C.

The 3-oxo 5α-compounds may be prepared by oxidation (e.g. using Jones reagent), of the corresponding 3α-hydroxy 5α-compounds.

5. Conversion of a N,N-disubstituted 11α-amine into a N-mono-substituted compound.

Compounds of formula (I) can be prepared from corresponding 11α-tertiary amino compounds by replacement of one of the groups by a hydrogen atom, e.g. by dealkylation using for example sodium nitrite followed by catalytic hydrogenolysis.

Thus, in particular, the compounds may be prepared by deprotection of a corresponding 11α-(protected amino) compound, having a substituent $R^1$ in addition to the protecting group, which may be, for example an acyl group such as a trichloroethoxycarbonyl, trifluoroacetyl, formyl, or a silyl, e.g. a trimethylsilyl group. An acyl group may be removed by hydrolysis e.g. with acid or alkali. The trichloroethoxycarbonyl group may also be removed by reduction with, for example, zinc and acetic acid. Alternatively an arylmethyl protecting group such as a benzyl group may be removed by catalytic hydrogenation to produce the unprotected 11α-mono substituted amino compound. A silyl group may be removed by e.g. solvolysis, with water (optionally containing acid or base) or an alcohol, or by treatment with a fluoride such as tetrabutylammonium fluoride.

This method may also be used to prepare compounds of formula (II) in which $R^3$ is hydrogen, by deprotection of a corresponding 11α-(protected amino) compound to yield a free 11α-amino group.

6. Esterification of a corresponding 17β-carboxylic acid.

Compounds of formula (I) may be prepared by reacting the corresponding compound of formula (II) in which $R^4$ is hydrogen or a reactive derivative thereof (e.g. an acid halide or anhydride or a salt) with the appropriate alcohol or alkyl or cycloalkyl halide. This reaction is preferably carried out at temperatures of −20° C. to +110° C., as is described for example in our British Patent Specification 1380246.

Where an alcohol is used in the esterification reaction, a coupling agent may be employed, for example a carbodiimide such as dicyclohexylcarbodiimide, preferably in the presence of a catalyst such as 4-dimethylaminopyridine.

Alternatively, esterification may be effected using a diazoalkane such as diazomethane.

Compounds of formula (II) in which $R^4$ is hydrogen can conveniently be formed by oxidising the corresponding 17β-acetyl compound, i.e. a pregnan-20-one, using for example NaOBr in an aqueous inert solvent (e.g. dioxan).

Compounds of formula (II) in which $R^4$ is a hydrogen atom may be prepared from their corresponding esters, for example by hydrolysis under acidic or basic conditions. Examples of suitable acids for such hydrolysis include mineral acids such as hydrochloric acid; examples of suitable bases include alkali metal hydroxides and carbonates, such as sodium or potassium hydroxides or carbonates.

When using certain of the above reagents, for example alkyl halides, it may be necessary to protect the 11α-amino group, for example as a trichloroethoxycarbonyl derivative.

7. Reduction of a corresponding $\Delta^{16}$-compound. The reduction may be effected by hydrogenation in the presence of a catalyst (e.g. a palladium catalyst) in a suitable solvent (e.g. an alcohol, ether or ester). The reaction may be effected conveniently at or about room temperature and atmospheric pressure in the presence of a tertiary base, e.g. triethylamine, and/or an acid, e.g. acetic acid.

The starting materials may be prepared by reaction of the corresponding 17-oxo compound with aqueous hydrogen cyanide to produce the 17-cyanohydrin which may be dehydrated to produce the $\Delta^{16}$-17β-cyano compound. This yields on hydrolysis the $\Delta^{16}$-17β-carboxylic acid and if required alkylation yields the corresponding $\Delta^{16}$-17β-carboxylic acid ester.

8. Compounds of formula (I) may also be prepared by transesterification i.e. by reaction of a corresponding compound having a 17β-ester group with an alcohol of formula $R^2OH$ in the presence of an acid or base catalyst at any temperature from room temperature to reflux, conveniently from 50° to 100° C., so as to prouce a compound of formula (I) hving a different 17β-ester group from the starting material; normally an excess of alcohol is used. Examples of suitable acid catalysts include mineral acids e.g. sulphuric and hydrochloric, and examples of suitable base catalysts include alkali metal hydroxides and carbonates, e.g. sodium or potassium hydroxides or carbonates.

9. The compounds of formula (I) may further be prepared by inversion of derivatives of the corresponding 3α-hydroxy compounds. The starting material may be a corresponding compound possessing a readily displaceable 3α-group such as a hydrocarbylsulphonyloxy (e.g. p-toluenesulphonyloxy or methanesulphonyloxy) group, and the 3α-group may be displaced by hydrolysis (e.g. under acidic conditions) to give the desired 3β-hydroxy compound.

10. Deprotection of a corresponding compound having a protected 3β-hydroxy group.

Compounds corresponding to compounds of formula (I) but containing protected (e.g. esterified or etherified) 3β-hydroxy groups may be formed where a 3β-hydroxy group is deliberately protected or where esterification of etherification of a 3β-hydroxy group takes place under the same conditions as a reaction elsewhere in the molecule.

An ester (e.g. alkanoyloxy) group may be hydrolysed to give the desired 3β-hydroxy compound under mild acidic or basic conditions. Weakly basic conditions are generally most convenient (using for example an alkali metal bicarbonate in aqueous methanol at any suitable temperature up to reflux). Dilute mineral acids (e.g. perchloric acid in aqueous methanol) may also be used.

An ether (e.g. tetrahydropyranyl ether) protecting group may be removed by treatment with an aqueous acid and a nitro-oxy protecting group by reduction, for example using zinc and acetic acid.

11. Salt formation.

Acid addition salts may be prepared by reaction of the free base with a suitable acid.

Base salts of compounds of formula (II) wherein $R^4$ is hydrogen may be prepared by the reaction of the free acid with a suitable base. For example, alkali metal salts may be prepared by reaction with an alkali metal hydroxide, carbonate, bicarbonate or 2-ethylhexanoate.

The methods indicated above for preparing the compounds of the invention can be used as the last main step in a preparative sequence. The same general methods can be used for the introduction of the desired groups at an intermediate stage in the stepwise formation of the required compound, and it will be appreciated that these general methods can be combined in many different ways in such multi-stage processes. Thus for example the desired 11α-amino group may be formed either before or after the reduction of a 3-oxo group. The sequence of the reactions in multi-stage processes should of course be chosen so that the reaction conditions used do not affect groups in the molecule which are desired in the final product.

The D-homo analogues of the compounds of the invention having a group —$CO_2R^2$ or —$CO_2R^4$ at the 17aβ-position may be prepared by essentially similar methods, using appropriate starting materials of the required structure.

The 3α-hydroxy steroids corresponding to the compounds of the invention, and which may be used as starting materials in certain of the processes set out above, may be prepared from 11-oxo-3α-hydroxy-5α-pregnan-20-one by oxidation to introduce a 17β-carboxyl group and introduction of the 11α-amino group as described above.

The compounds of formula (I), their D-homo analogues and physiologically acceptable acid addition salts thereof may be formulated for administration in any convenient way, and the invention therefore includes within its scope pharmaceutical compositions comprising a compound of formula (I) or a physiologically acceptable salt thereof in admixture with pharmaceutical carriers or excipients.

The compounds and their physiologically acceptable salts may for example be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, mucilage of starch or polyvinylpyrrolidone; fillers, for example lactose, sugar, maize-starch, calcium phosphate or sorbitol; lubricants, for example magnesium stearate, talc, polyethylene glycol or silica; disintegrants, for example potato starch or sodium starch glycollate; or acceptable wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The compounds or their salts may also be formulated as suppositories, e.g. containing conventional suppository bases such as cocoa butter or other glycerides.

The compounds of formula (I), their D-homo analogues, and physiologically acceptable acid addition salts thereof may also be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

When the compositions comprise dosage units, each unit will preferably contain 10–1000 mg of the active ingredient advantageously 25–500 mg. The daily dosage as employed for adult human treatment will preferably range from 25–2500 mg preferably 50–1000 mg depending on the route and frequency of administration. The compounds may be given in divided doses, for example 1–4 times per day.

The antidysrhythmic compounds according to the invention may be administered in combination with other therapeutic agents.

The following Examples illustrate the invention.

Melting points were determined in capillaries and are corrected. Optical rotations were determined at room temperature on 1% solutions in chloroform.

Preparative t.l.c. and column chromatography were carried out on silica.

Petrol refers to petroleum ether b.p. 60°–80° C.

Solutions were dried using anhydrous sodium sulphate.

IR spectra were determined in bromoform and refer to the carbonyl stretching frequency of the 17β-carboxylic acid ester group.

Chloroiridic acid reagent was prepared by refluxing a mixture of chloroiridic acid (50 mg), isopropanol (94 ml), water (6 ml) and trimethylphosphite for 24 hours and adjusting to pH7 by the addition of triethylamine immediately prior to use.

Jones reagent was prepared from chromium trioxide (26.8 g) and concentrated sulphuric acid (23.0 ml) diluted to 100 ml with water.

PREPARATION 1

11α-(2,2,2-trichloroethoxycarbonylamino)-3α-(2,2,2-trichloroethoxycarbonyloxy)-5α-pregnan-20-one A solution of 11α-amino-3α-hydroxy-5α-pregnan-20-one (19.5 g) in dichloromethane (250 ml) and pyridine (26.5 ml) was cooled in an ice-bath during the addition of 2,2,2-trichloroethyl chloroformate (36 ml). On complete addition, water was carefully added and when no further reaction occurred the mixture was washed with 2 M-HCl solution (×2) and water. The solution was dried and evaporated to leave an oil (24.6 g) which was treated with ether to give the title compound (14.1 g) as a solid.

PREPARATION 2

3α-Hydroxy-11α-(2,2,2-trichloroethoxycarbonylamino)-5α-androstane-17β-carboxylic acid Bromine (3.85 ml) was added dropwise to a solution of sodium hyroxide (11 g) in water (85 ml) keeping the temperature at −10° C. Dioxan (42 ml) was added and the mixture was slowly added to a stirred solution of the product of Preparation 1 (15.5 g) in dioxan (280 ml) and water (85 ml) at 10° C. After complete addition the mixture was stirred for 2.5 h. Na$_2$SO$_3$ (4 g) was added and after 0.5 h the mixture was brought to pH 2 with 2 M-HCl solution. Water (500 ml) was added and the mixture was extracted with chloroform (×2). The extract was washed with water, dried and evaporated to leave a froth (9.5 g) which was purified by column chromatography eluted with EtOAc/petrol (1:1) to give the title compound (4.73 g). A portion was crystallised from ether/petrol, m.p. dec(gas evolved) 100° C., $[\alpha]_D + 19°$.

PREPARATION 3

Methyl 3α-hydroxy-11α-(2,2,2-trichloroethoxycarbonylamino)-5α-androstane-17β-carboxylate A solution of the product of Preparation 2 (4 g) in DMF (80 ml) was stirred with K$_2$CO$_3$ (3.7 g) at 0° C. Methyl iodide (2.6 ml) was added and the mixture was stirred for 2 h. Water (300 ml) was added and the mixture was extracted with ether (×3). The extract was washed with water, dried and evaporated to leave a froth which was purified by column chromatography eluted with EtOAc/petrol (1:2) and crystallised from ether to give the title compound (2.45 g), m.p. 167°–170° C., $[\alpha]_D + 25°$.

PREPARATION 4

11α-(2,2,2-Trichloroethoxycarbonylamino)-3α-[2,2,2-trichloroethoxycarbonyloxy]-5β-pregnan-20-one Pyridine (39 ml) and 2,2,2-trichloroethyl chloroformate (53 ml) were added to an ice-cooled solution of 11α-amino-3α-hydroxy-5β-pregnan-20-one (26.54 g) in dichloromethane (350 ml). After 2 h water (400 ml) was added and the organic phase was separated and evaporated to leave a brown oil which crystallised on trituration with ether/petrol to give the title compound (47.86 g), m.p. 174°–176° C., $[\alpha]_D + 60°$.

PREPARATION 5

3α-Hydroxy-11α-(2,2,2-trichloroethoxycarbonylamino)-5β-androstane-17β-carboxylic acid Bromine (12.5 ml) was added to a solution of sodium hydroxide (35.1 g) in water (270 ml) keeping the temperature between −5° and 0° C. Dioxan (135 ml) was added and this mixture was added to a stirred solution of the product of Preparation 4 (47 g) in dioxan (900 ml) and water (270 ml) at 10° C. After 1 h sodium sulphite (12 g) was added and the mixture was diluted with water, brought to pH 2 with concentrated HCl solution and extracted with chloroform (×2). The extract was washed with water (×2), dried and evaporated to leave an oil which was taken up in dioxan. 2 M-NaOH solution was added to give a pH <11 and the mixture was stirred for 3 h. The mixture was brought to pH 2 with concentrated HCl solution and diluted with water. The precipitate was extracted with chloroform (×2) and the extract was washed with water, dried and evaporated to leave an oil which crystallised from ether/petrol to give the title compound (22.5 g), m.p. 250°–251° C., $[\alpha]_D + 34°$,

PREPARATION 6

Methyl 3α-hydroxy-11α-(2,2,2-trichloroethoxycarbonylamino)-5β-androstane-17β-carboxylate Potassium carbonate (19.606 g) and methyl iodide (13.75 ml) were added to a stirred solution of the product of Preparation 5 (21.9 g) in dimethylformamide (400 ml) at 0° C. After 1.5 h the mixture was diluted with water (1.5 l) and extracted with ethyl acetate (×2). The extract was washed with brine (×2), dried and evaporated to leave the title compound (23.07 g) as a froth, $[\alpha]_D + 30°$.

PREPARATION 7

Methyl 11α-amino-3α-hydroxy-5α-androstane-17β-carboxylate

A solution of the product of Preparation 3 (2.4 g) in glacial acetic acid (25 ml) was stirred with zinc (2.5 g) for 4 hours. The zinc was removed by filtration and washed with water (50 ml) and ether (50 ml). The filtrate and washings were brought to pH 10 with 0.88 NH$_3$ solution and extracted with ether (×4). The extract was washed with water, dried and evaporated to leave a solid (1.65 g). A portion was crystallised from ether to give the title compound, m.p. 113°–116°, $[\alpha]_D + 38°$

PREPARATION 8

Methyl 11α-cyclopentylamino-3α-hydroxy-5α-androstane-17β-carboxylate

A solution of the product of Preparation 7 (2 g) in ethanol (20 ml) was treated with cyclopentanone (2 ml) and sodium cyanoborohydride (2 g) for 18 h. Incomplete reduction was found and sodium borohydride (0.05 g) was added. After 1 h the mixture was diluted with 5% NaHCO₃ solution (20 ml) and water (60 ml) and the precipitate was extracted with ether (×3). The extract was washed with water, dried and evaporated to leave an oil which was purified by column chromatography and preparative t.l.c. using chloroform:methanol; (9:1) to give the title compound (1.47 g) as a froth, $[\alpha]_D+12°$, $\nu_{max}$ 1724 cm$^{-1}$.

PREPARATION 9

Methyl 11α-amino-3α-hydroxy-5β-androstane-17β-carboxylate

Zinc powder (52.5 g) was added to a stirred solution of the product of Preparation 6 (22 g) in glacial acetic acid (600 ml). After 20 h the zinc was removed by filtration and washed with water. The filtrate and washings were evaporated to low bulk and then brought to pH 10 with 0.88 NH₃ solution. The oily precipitate was extracted with ethyl acetate (×2). The extract was washed with brine (×2), dried and evaporated to leave the title compound (13.56 g) as a froth $[\alpha]_D+36°$.

PREPARATION 10

Methyl 3α-hydroxy-11α-(3-methylbutylamino)-5β-androstane-17β-carboxylate

Potassium carbonate (8.65 g) and 1-iodo-3-methylbutane (6.5 ml) were added to a stirred solution of the product of Preparation 9 (6 g) in dioxan (100 ml) and the mixture was heated at reflux for 50 h. Water (300 ml) was added to the cooled mixture and concentrated HCl solution was added to bring the pH to 2. The mixture was washed with ether and the ether wash was extracted with water (×4). The total aqueous phase was brought to pH 10 with 0.88 NH₃ solution and the precipitation was extracted with ether (×2). The extract was washed with brine (×2), dried and evaporated to leave a froth (5.6 g). A sample (1.16 g) was purified by preparative t.l.c. using chloroform:methanol (9:1) to give the title compound (0.548 g), $[\alpha]_D+8°$, $\nu_{max}$ 1726 cm$^{-1}$.

PREPARATION 11

Methyl 11α-(3-methylbutylamino)-3-oxo-5β-androstane-17β-carboxylate

Jones reagent (8 ml) was added dropwise to a stirred solution of the product of Preparation 10 (4 g) in acetone (300 ml). After 2 h the mixture was diluted with water (500 ml) and brought to pH 10 with 0.88 NH₃ solution. The mixture was extracted with ether and filtered before separation of the organic phase. The aqueous phase was further extracted with ether and the total extract was washed with water (×2), dried and evaporated to leave the title compound (3.198 g) as an oil $[\alpha]_D+3°$.

PREPARATION 12

Methyl 11α-cyclopentylamino-3-oxo-5α-androstane-17β-carboxylate

Jones reagent was added dropwise to a stirred solution of the product of Preparation 8 (1.4 g) in acetone (120 ml) until the reagent colour was not discharged. The mixture was brought to pH 10 with 0.88 NH₃ solution and diluted with water (300 ml). The precipitate was extracted with ether (×3) and the extract was washed with water, dried and evaporated to leave a solid (1.4 g). A portion (0.2 g) was crystallised from ether to give the title compound (0.12 g), m.p. 156°-158° C., $[\alpha]_D-3°$.

PREPARATION 13

Methyl 3-oxo-11α-(2,2,2-trichloroethoxycarbonylamino)-5α-androstane-17β-carboxylate Jones reagent was added dropwise to a stirred solution of the product of Preparation 3 (0.3 g) in acetone (20 ml) until the reagent colour was not discharged. Water (150 ml) was added and the precipitate obtained was collected by filtration, washed with water, dried and crystallised from ethyl acetate/petrol to give the title compound (0.19 g), m.p. 208°-209° C., $[\alpha]_D+41°$.

PREPARATION 14

Methyl 3β-hydroxy-11α-(2,2,2-trichloroethoxycarbonylamino)-5α-androstane-17β-carboxylate Sodium borohydride (1 g) was added to a solution of the product of Preparation 13 (12 g) in methanol (200 ml). After 15 min the mixture was slowly diluted with water to 1.5l. The solid (11.2 g) was collected by filtration, washed with water, dried and crystallised from aqueous methanol to give the title compound (8.12 g), m.p. 140°-143° C., $[\alpha]_D 8°$.

PREPARATION 15

Methyl 11α-amino-3β-hydroxy-5α-androstane-17β-carboxylate

Zinc (10 g) was added to a stirred solution of the product of Preparation 14 (10.5 g) in glacial acetic acid (50 ml) for 4 h. The zinc was removed by filtration and washed with water (10 ml). The filtrate and washings were brought to pH 11 with 50% NaOH solution and extracted with ether (×3). The extract was washed with water, dried and evaporated to leave a froth (5.81 g). A portion (0.5 g) was purified by preparative t.l.c. using 2% NH₃ solution in methanol to give the title compound (0.382 g), $[\alpha]_D+34°$, $\nu_{max}$ 1720 cm$^{-1}$.

PREPARATION 16

Methyl 11α-cyclohexylamino-3α-hydroxy-5β-androstane-17β-carboxylate

Cyclohexanone (2.9 ml) and sodium cyanoborohydride (2.512 g) were added to a stirred solution of the product of Preparation 9 (2.505 g) in ethanol (30 ml). After 5 h the mixture was diluted with 5% NaHCO₃ solution and extracted with ether (×2). The extract was washed with water (×2), dried and evaporated to leave a froth (2.544 g). A sample (0.39 g) was purified by preparative t.l.c. using CHCl₃:MeOH (19:1) to give the title compound (0.27 g), $[\alpha]_D-9°$, $\nu_{max}$ 1725 cm$^{-1}$.

PREPARATION 17

Methyl 11α-cyclohexylamino-3-oxo-5β-androstane-17β-carboxylate

Jones reagent (4.25 ml) was added dropwise to a stirred solution of the product of Preparation 16 (2.164 g) in acetone (150 ml) until the reagent colour was not discharged. After 2.5 h the mixture was diluted with water (300 ml) and brought to pH 10 with 0.88 NH₃ solution. The mixture was shaken with ether (250 ml) and the total liquid was filtered. The aqueous phase was separated and extracted with ether (250 ml). The combined organic phase was washed with water ($\times 2$), dried and evaporated to leave an oil (1.119 g). A portion (0.32 g) was purified by preparative t.l.c. using CHCl$_3$:MeOH (19:1) to give the title compound (0.19 g) $[\alpha]_D -9°$, $\nu_{max}$ 1710 cm$^{-1}$, 1725 cm$^{-1}$.

PREPARATION 18

Methyl 11α-cyclohexylamino-3α-hydroxy-5α-androstane-17β-carboxylate

Sodium cyanoborohydride (2 g) was added to a mixture of the product of Preparation 7 (2 g) and cyclohexanone (2.5 ml) in ethanol (30 ml). The mixture was kept at 21° C. for 5 h. 5% NaHCO$_3$ solution and water were added and the mixture was extracted with ether ($\times 2$). The extract was washed with water, dried and evaporated to leave a froth which was purified by column and preparative layer chromatography using CHCl$_3$:MeOH (9:1) to give the title compound (0.763 g) as a froth, $[\alpha]_D +6°$, $\nu_{max}$ 1720 cm$^{-1}$.

PREPARATION 19

Methyl 11α-cyclohexylamino-3-oxo-5α-androstane-17β-carboxylate

Jones reagent was added dropwise to a stirred solution of the product of Preparation 18 (3.095 g) in acetone (225 ml) until the reagent colour was not discharged. After 2.5 h the mixture was diluted with water (300 ml) and brought to pH 10 with 0.88 NH$_3$ solution. The mixture was shaken with ether (250 ml) and the total liquid was filtered. The aqueous phase was separated and extracted with ether (250 ml) and the combined organic phase was washed with water ($\times 2$), dried and evaporated to leave an oil (2.099 g). A sample (0.5 g) was purified by preparative t.l.c. using CHCl$_3$:MeOH (19:1) and crystallised from petrol to give the title compound (0.19 g) m.p. 91°–93° C., $[\alpha]_D -14°$.

EXAMPLE 1

Methyl 11α-cyclopentylamino-3β-hydroxy-5α-androstane-17β-carboxylate

Sodium borohydride (0.3 g) was added to a solution of the product of Preparation 12 (1.2 g) in methanol (100 ml). The mixture was left for 1.5 h and water (500 ml) was added. The precipitate formed was extracted with ether ($\times 3$) and the extract was washed with water, dried and evaporated to leave an oil (1.17 g) which was purified by column and preparative layer chromatography using CHCl$_3$:MeOH (9:1) to give the title compound (0.512 g), which crystallised from petrol, m.p. 143°–145° C., $[\alpha]_D +3°$.

EXAMPLE 2

Methyl 3β-hydroxy-11α-(3-methylbutylamino)-5α-androstane-17β-carboxylate

The product of Preparation 15 (5.2 g) was dissolved in ethanol (100 ml) and the solution was stirred and heated at reflux with 1-bromo-3-methyl-butane (10 ml), potassium carbonate (7 g) and sodium iodide (0.2 g) for 72 h. (200 ml) was added and the mixture was extracted with ether ($\times 3$). The extract was washed with water, dried and evaporated to leave an oil which was purified by column chromatography on silica (200 g) eluted with CHCl$_3$:MeOH (19:1) to give an oil. A portion was further purified by preparative t.l.c. using ether to give an oil.

The oil (0.62 g) was dissolved in methanol (30 ml) and the solution was heated at reflux with concentrated H$_2$SO$_4$ (2.5 ml) for 18 h. The cooled mixture was brought to pH 11 with 50% NaOH solution and diluted with water (100 ml). The precipitate was extracted with ether ($\times 3$). The extract was washed with water, dried and evaporated to give the title compound (0.6 g), $[\alpha]_D +10°$, $\nu_{max}$ 1720 cm$^{-1}$.

EXAMPLE 3

Methyl 11α-cyclohexylamino-3β-hydroxy-5β-androstane-17β-carboxylate

The product of Preparation 17 (0.78 g) was dissolved in chloroiridic acid reagent (27 ml) and the solution was heated at reflux for 24 h. The mixture was cooled and diluted with water to give an oily suspension which was extracted with ether ($\times 2$). The extract was washed with water ($\times 5$), dried and evaporated to leave a froth (0.694 g) which was purified by preparative t.l.c. using CHCl$_3$:MeOH (9:1) to give the title compound (0.369 g), $[\alpha]_D -18°$, $\nu_{max}$ 1722 cm$^{-1}$.

EXAMPLE 4

Methyl 11α-cyclohexylamino-3β-hydroxy-5α-androstane-17β-carboxylate

Sodium borohydride (0.137 g) was added to a solution of the product of Preparation 19 (1.587 g) in methanol (20 ml) and the mixture was left for 1.5 h. Water (75 ml) was added and the resultant precipitate was extracted with ether ($\times 2$). The extract was washed with water ($\times 2$), dried and evaporated to leave a froth (1.362 g) which was purified by preparative t.l.c. using CHCl$_3$:MeOH (9:1) to give the title compound (0.709 g), $[\alpha]_D -6°$, $\nu_{max}$ 1725 cm$^{-1}$.

EXAMPLE 5

Methyl 3β-hydroxy-11α-(3-methylbutylamino)-5β-androstane-17β-carboxylate

The product of Preparation 11 (1.745 g) was dissolved in chloroiridic acid reagent (44 ml) and the mixture was heated at reflux for 18 h. Water was added to the cooled mixture and the precipitate was extracted with ether ($\times 2$). The extract was washed with water ($\times 2$), dried and evaporated to leave a froth (1.6 g) which was purified by preparative t.l.c. using chloroform:methanol (9:1) to give the title compound (0.759 g), $[\alpha]_D -3°$, $\nu_{max}$ 1724 cm$^{-1}$.

EXAMPLES 6–10

Table 1 summarises the preparation of the hydrochloride salts.

A solution (0.0979 M) of hydrochloric acid in water was added to the base or a suspension of the base in any additional water and the mixture was stirred or shaken until a clear solution was obtained. The mixture was made up to the appropriate volume with water and the pH was measured.

TABLE 1

| Ex. No. | Ex. No. of Free Base | Wt (mg) | HCl vol. (ml) | Additional Water (ml) | Total Vol (ml) | pH | Conc'n (%) |
|---|---|---|---|---|---|---|---|
| 6 | 1 | 100 | 2.45 | — | 10 | 3.1 | 1 |
| 7 | 2 | 100 | 2.43 | 5 | 10 | 3.0 | 1 |
| 8 | 3 | 100 | 2.37 | 5 | 10 | 2.6 | 1 |
| 9 | 4 | 200 | 4.73 | 3 | 10 | 2.5 | 2 |
| 10 | 5 | 100 | 2.44 | 26 | 33 | 3.6 | 0.3 |

EXAMPLE 11

Methyl 3β-hydroxy-11α-(3-methylbutylamino)-5α-androstane-17β-carboxylate hydrochloride 3-Methylbutanal (1.3 ml) then sodium cyanoborohydride (258 mg) were added to a stirred solution of the product of Example 2 (3.20 g). The solution was stirred for 15 min then sodium borohydride (446 mg) was added. After a further 75 min water (300 ml) was added and the mixture was extracted with ethyl acetate (×2). The combined extracts were washed with saturated brine, dried and evaporated to a viscous white foam (3.70 g). This was dissolved in chloroform (10 ml) and a mixture of concentrated hydrochloric acid (0.94 g) and ethyl acetate (15 ml) was added. Crystallisation commenced immediately and after brief refrigeration the crystals were collected, washed with cold chloroform-ethyl acetate (2:3, 25 ml) and dried to give the title compound as white needles (1.95 g), m.p. 282°–285°, [α]$_D$+23°. The liquors and washings were evaporated to dryness and the residue stirred with ethyl acetate (30 ml) to give additional crystalline material which was collected and dried (1.65 g), m.p. 275°–280°, [α]$_D$+26°.

The following Examples illustrate pharmaceutical formulations of the compounds according to the invention.

EXAMPLE A

| Tablet - Wet granulated | mg/tablet |
|---|---|
| Methyl-3β-hydroxy-11α-(3-methylbutyl-amino)-5α-androstane-17β-carboxylate hydrochloride | 108.00 |
| Maize starch | 126.00 |
| Polyvinyl pyrrolidone | 2.3 |
| Sodium starch glycolate | 6.8 |
| Magnesium stearate | 1.9 |
| Tablet weight | 245.00 |

Sieve the steroid and maize starch through a 40 mesh screen. Blend the maize starch with the steroid in a suitable blender. Make a 5–10% w/v aqueous solution of the polyvinyl pyrrolidone. Add this solution to the mixing powder and mix until granulated. Pass the granulate through a number 12 screen. Dry the granules at 50° C. in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine.

EXAMPLE B

Intravenous Injections

Ingredients:

Methyl-3β-hydroxy-11α-(3-methylbutylamino)5α-androstane-17β-carboxylate hydrochloride (equivalent to 1 to 10 mg of free base). Sodium chloride-sufficient for isotonicity. Water for Injection to 1 ml.

Dissolve the steroid and the sodium chloride in some of the water. If necessary adjust the pH with sodium hydroxide solution or hydrochloric acid solution. Make up to volume with water and stir until homogeneous. Filter the solution into clean glass vials and seal by fusion. The solution may be sterilised by autoclaving or filtration or preparing under aseptic conditions.

We claim:

1. Compounds of the formula

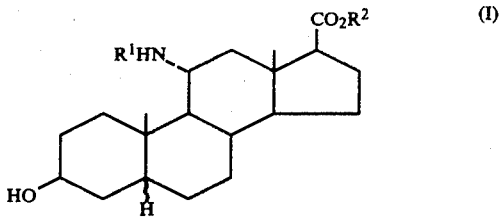

wherein R$^1$ is a C$_{1-8}$ alkyl group or a C$_{3-7}$ cycloalkyl group and R$^2$ is a C$_{1-6}$ alkyl group or a C$_{3-6}$ cycloalkyl group and the D-homo analogues thereof having the group —CO$_2$R$^2$ (wherein R$^2$ is as defined above) at the 17αβ-position, and acid addition salts thereof.

2. Compounds as claimed in claim 1 wherein R$^1$ is an isopentyl or cyclohexyl group and R$^2$ is a methyl or ethyl group, having a 5α-hydrogen atom and wherein ring D has five members.

3. A compound as claimed in claim 1 in the form of physiologically acceptable acid addition salts.

4. Compounds as claimed in claim 3 in the form of hydrochloride, hydrobromide, phosphate, sulphate, p-toluenesulphonate, methanesulphonate, citrate, tartrate, acetate, ascorbate, lactate, maleate, succinate, tricarbyllate, glutarate and glutaconate acid addition salts.

5. A compound according to claim 1, which is methyl 3β-hydroxy-11α-(3-methylbutylamino)-5β-androstane-17β-carboxylate and its physiologically acceptable acid addition salts.

6. A compound according to claim 1, which is methyl 3β-hydroxy-11α-(3-methylbutylamino)-5α-androstane-17β-carboxylate and its physiologically acceptable acid addition salts.

7. A compound according to claim 1, which is methyl 11α-cyclopentylamino-3β-hydroxy-5α-androstane-17β-carboxylate and its physiologically acceptable acid addition salts.

8. A compound according to claim 1, which is methyl 11α-cyclohexylamino-3β-hydroxy-5β-androstane-17β-carboxylate and its physiologically acceptable acid addition salts.

9. Pharmaceutical compositions comprising at least one compound of formula (I) or D-homo analogue thereof as claimed in claim 1 or a physiologically acceptable acid addition salt thereof in admixture with one or more pharmaceutical carriers or excipients.

10. A process for the manufacture of a compound as claimed in claim 1 which process comprises one or more of the following steps:

(A) reacting a corresponding 11α-amino compound or a corresponding 11α-amino 17β- (or 17αβ-) carboxylic acid compound with a compound of formula R$^1$X (wherein R$^1$ is as defined in claim 1 and X is a readily displaceable atom or group);

(B) reacting a corresponding 11α-amino compound in the presence of a reducing agent with a monocarbonyl compound serving to introduce the group $R^1$ (wherein $R^1$ is as defined in claim 1);

(C) reducing with a suitable reducing agent a corresponding 3-oxo compound;

(D) converting a corresponding N,N-disubstituted 11α-amino compound into an N-monosubstituted compound;

(E) esterifying a corresponding 17β- (or 17αβ-) carboxylic acid;

(F) reacting a corresponding $\Delta^{16}$-compound with a suitable reducing agent;

(G) transesterifying a corresponding compound having a 17β- (or 17αβ-) group other than the desired group —COOR$^2$ (wherein $R^2$ is as defined in claim 1) with an alcohol of formula $R^2OH$ (wherein $R^2$ is as defined in claim 1);

(H) inverting a corresponding 3α-hydroxy compound;

(I) deprotecting a corresponding compound having a protected 3β-hydroxy group; and (J) converting a compound of formula (I), or a D-homo analogue thereof into an acid addition salt thereof.

11. Compounds of the formula

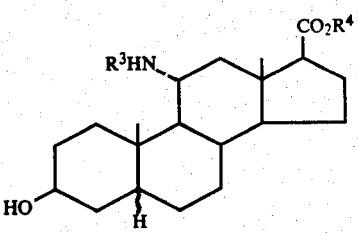

(II)

wherein $R^3$ is a hydrogen atom, a $C_{1-8}$ alkyl group or a $C_{3-7}$ cycloalkyl group, and $R^4$ is a hydrogen atom, a $C_{1-6}$ alkyl group or a $C_{3-6}$ cycloalkyl group with the proviso that at least one of $R^3$ and $R^4$ is a hydrogen atom and the D-homo analogues thereof having the group —CO$_2$R$^4$ (wherein $R^4$ is as defined above) at the 17αβ-position, and salts and zwitterionic forms thereof.

12. A method of therapy or prophylaxis of a human or animal body suffering from or liable to cardiac dysrhythmias which method comprises administering to the said body an effective amount of a compound of formula (I), a D-homo analogue thereof, or a physiologically acceptable acid addition salt thereof as claimed in claim 1.

13. Compounds of formula (I), a D-homo analogue thereof, or a physiologically acceptable acid addition salt thereof as claimed in claim 1 for use in a method of treatment of the human or animal body to combat cardiac dysrhythmias therein.

* * * * *